United States Patent [19]

Isa et al.

[11] 4,244,882
[45] Jan. 13, 1981

[54] PROCESS FOR CONTINUOUS PRODUCTION OF FULL ESTERS OF POLYOLS

[75] Inventors: Hiroshi Isa, Yachiyo; Kenji Karube, Toride; Junichi Nakayama, Chiba, all of Japan

[73] Assignees: The Lion Fat & Oil Co., Ltd.; Mitsubishi Chemical Industries Ltd., both of Tokyo, Japan

[21] Appl. No.: 49,603

[22] Filed: Jun. 18, 1979

[30] Foreign Application Priority Data

Jun. 22, 1978 [JP] Japan ................................. 53/75698

[51] Int. Cl.³ ............................................. C07C 67/38
[52] U.S. Cl. .................................. 260/410.6; 560/233
[58] Field of Search ...................... 560/233; 260/410.6

[56] References Cited

U.S. PATENT DOCUMENTS

| 3,507,891 | 4/1970 | Hearne | 260/410.9 |
|---|---|---|---|
| 3,883,587 | 5/1975 | Isa | 560/233 |
| 3,891,683 | 6/1975 | Isa | 560/233 |
| 3,935,228 | 1/1976 | Keblys | 560/233 |
| 3,946,055 | 3/1976 | Isa | 560/233 |
| 3,974,194 | 8/1976 | Isa | 560/233 |
| 3,980,683 | 9/1976 | Isa | 560/233 |
| 4,041,057 | 8/1977 | Fanning | 560/233 |

FOREIGN PATENT DOCUMENTS

| 2504005 | 8/1975 | Fed. Rep. of Germany | 560/233 |
|---|---|---|---|
| 49-108013 | 10/1974 | Japan | 560/233 |
| 50-62925 | 5/1975 | Japan . | |
| 1269525 | 4/1976 | United Kingdom | 560/233 |

*Primary Examiner*—Natalie Trousof
*Assistant Examiner*—Michael Shippen
*Attorney, Agent, or Firm*—Armstrong, Nikaido, Marmelstein & Kubovcik

[57] ABSTRACT

Full esters of polyols selected from pentaerythritol and polypentaerythritols are continuously produced by (i) continuously introducing a solution of the polyols in pyridine bases, olefins having at least 4 carbon atoms in an amount of at least 0.4 equivalent per 1.0 equivalent of the hydroxyl group in the polyols, a catalyst containing cobalt carbonyls and pyridine bases, and carbon monoxide, into a reaction zone from one end thereof in such an amount of the pyridine bases as is within the range of from 40 to 70% by weight based on the total amount of the pyridine bases, the polyols and the olefins; (ii) introducing an additional amount of the olefins into at least one middle portion of the reaction zone, and; (iii) continuously withdrawing the resultant reaction mixture from the other end of the reaction zone.

9 Claims, 4 Drawing Figures

PROCESS FOR CONTINUOUS PRODUCTION OF FULL ESTERS OF POLYOLS

This invention relates to a process for continuously producing full esters of polyols by the reaction of polyols, such as pentaerythritol, dipentaerythritol, tripentaerythritol and the like, and olefins and carbon monoxide, in the presence of a catalyst comprising cobalt carbonyls and pyridine bases (e.g. pyridine and $\gamma$-picoline). More specifically, this invention relates to a process which is capable of producing full esters of polyols at a high efficiency, even when a reactor provided with no mechanical agitator, such as a bubble column (or a gas sparged column), is used.

By the term "full ester of polyol", as used herein, is meant the ester of polyol in which substantially all of the hydroxyl groups of the polyol (e.g. 97% or more of the hydroxyl groups, on the average, of the polyol) are esterified.

It is known in the art that esters of alcohols are produced by the reaction of alcohols, olefins and carbon monoxide in the presence of catalysts comprising cobalt carbonyls and pyridine bases. In accordance with such known processes, esters can be produced from various alcohols and olefins. For instance, in such known processes, the full esters of polyols, such as pentaerythritol, dipentaerythritol and the like, are produced from the polyols (please refer to, for example, U.S. Pat. Nos. 3,883,587, 3,891,683 and 3,946,055). These full esters of polyols are widely utilized as lubricants, plasticizers, surfactants and the like.

However, these known prior processes involve various problems which should be solved, from a practical point of view, when the full esters of polyols, such as pentaerythritol, are commercially manufactured. One of the problems is due to the facts that the polyols have high melting points and are not easily dissolved in conventional solvents. For this reason, it is not easy to continuously introduce the polyols into a reactor. Furthermore, since the polyols are separated in a separate phase (e.g. as a solid phase or a separated liquid phase), in a reactor, the use of a reactor provided with an agitator is required. The use of such reactor is expensive and, therefore, the process is not considered of high practical value in industry.

Accordingly, the objects of this invention are to obviate the above-mentioned problems in the known processes and to provide an improved process for continuously producing full esters of polyols by the reaction of polyols, olefins and carbon monoxide in the presence of cobalt carbonyls and pyridine bases, in a homogeneous reaction system, at a high productivity and a high yield of the full esters of polyols.

Another object of this invention is to provide an improved process for the continuous production of full esters of polyols, which process can be advantageously used in production of such esters on a commercial scale.

In accordance with this invention, there is provided a process for continuously producing full esters of polyols by the reaction of at least one polyol selected from pentaerythritol and polypentaerythritols, at least one olefin having at least 4 carbon atoms, and carbon monoxide, in the presence of a catalyst containing cobalt carbonyls and pyridine bases, comprising:

continuously introducing a solution of the polyol in the pyridine bases, the olefin in an amount of at least 0.4 equivalent per 1.0 equivalent of the hydroxyl group in the polyol, the cobalt carbonyls and the carbon monoxide, into a reaction zone from one end thereof in such an amount of the pyridine bases as is within the range of from 40 to 70% by weight, based on the total amount of the pyridine bases, the polyol and the olefin;

introducing an additional amount of the olefin into at least one middle portion of the reaction zone, and;

continuously withdrawing the resultant reaction mixture from the other end of the reaction zone.

The foregoing and other objects and advantages of this invention will become more apparent from the following description of the preferred embodiments of the invention, some of which description is set forth with reference to the accompanying drawings wherein.

Figure 1:
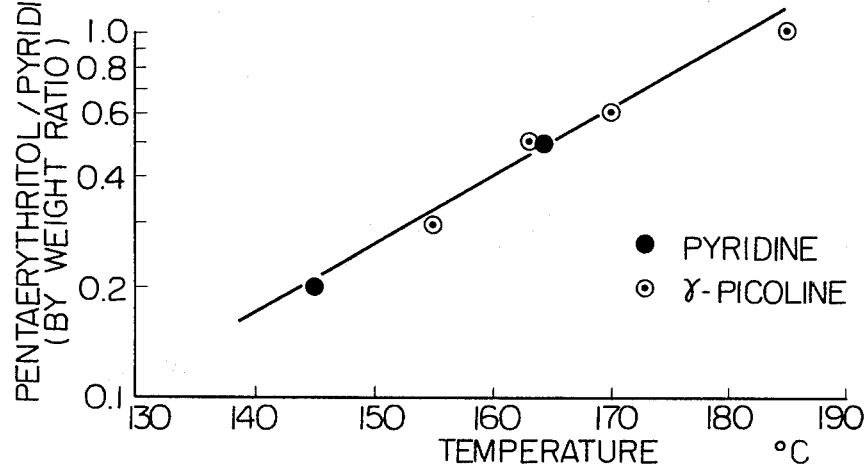
FIG. 1 is a graph illustrating the relationship between the solubility of pentaerythritol in pyridine and its derivative (i.e. $\gamma$-picoline) and temperature.

We have now found that the above-mentioned problems in the conventional processes are solved by handling the polyols as a solution, and that the polyols have a considerably high solubility with respect to the pyridine bases at an elevated temperature and, thus, that the polyols can be easily and continuously fed into a reactor by using the pyridine bases as a solvent for the polyols. However, since these polyols are slightly dissolved in olefins, the polyols are separated in a separate phase when olefins having at least 4 carbon atoms are added to a solution of polyols in the pyridine bases. For this reason, even when the polyols are fed into a reactor in the form of a solution in pyridine bases, the polyols are separated in the reactor as a separate phase if the olefins are simultaneously fed into the reactor. This separation of the polyols from the solution due to the addition of the olefins can be mitigated either by the reduction of the concentration of the polyols in the solution in pyridine bases or by the reduction of the additional amount of the olefins. However, the reduction of the polyol concentration in the solution results in a decrease in the yield of the ester per unit volume of the reactor. In the case where the reaction is carried out at a constant ratio of the cobalt to the polyols, the reaction rate itself is liable to be decreased, due to the fact that the ratio of the pyridine bases to the cobalt becomes too high. On the other hand, the reduction of the additional amount of the olefins causes not only a decrease in the reaction rate, but also a decrease in the selectivity of the full esters of the polyols.

After studying, in detail, the esterification reaction of the polyols, the present inventors have found the fact that the solubility of the polyols in the pyridine bases remarkably increases as the esterification reaction of the polyols proceeds and, therefore, the homogeneous solution state can be maintained even when a large amount of the olefins coexists in the system. Therefore, when the esterification reaction of polyols is commenced by the addition of olefins to the solution of the polyols in pyridine bases in such a small amount that the polyols do not separate from the solution as a separate phase, and then, an additional amount of the olefins is fed to the reaction mixture after the esterification reaction has started to proceed, the esterification reaction can be carried out in a homogeneous solution state, and further, a high productivity and high yield of the full esters can be achieved.

For example, the above described process has been carried out by the inventors in the following manners. An autoclave provided with an agitator was charged with pentaerythritol, hexene-1, γ-picoline and an activated catalyst solution in such amounts that the molar ratio of the hexene-1 to the pentaerythritol was 2.5, the molar ratio of the γ-picoline to the pentaerythritol was 5.4 and, further, the ratio of the cobalt (in terms of metallic cobalt) to the pentaerythritol was 0.12 (gram atom/mol). The activated catalyst solution was prepared as follows. Cobalt octanoate, γ-picoline and water were first charged, in a molar ratio of 1.3:9:2, respectively, into an autoclave provided with an agitator and were heated at a temperature of 170° C. The autoclave was then pressurized with carbon monoxide to a total pressure of 200 kg/cm$^2$G, while the contents of the autoclave were agitated for 2 hours, to obtain the activated catalyst.

Figure 4:
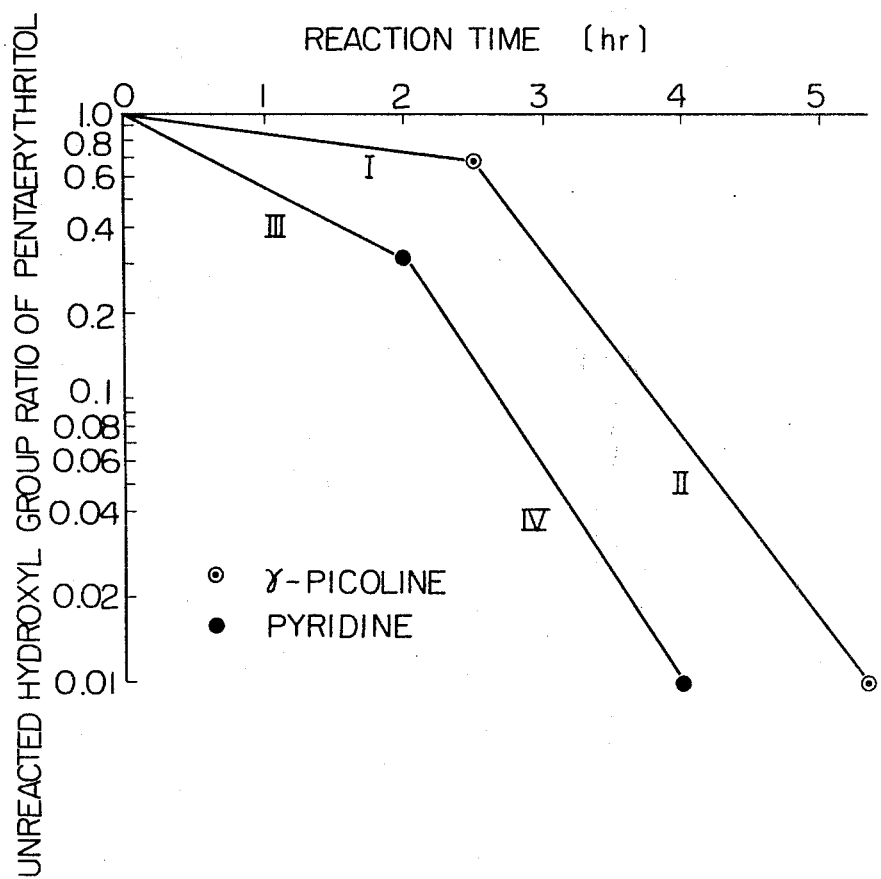
FIG. 4 is a graph illustrating the course of the reaction when pentaerythritol, hexene-1 and carbon monoxide are reacted with each other in pyridine bases in the presence of the cobalt catalysts.

The reaction mixture of pentaerythritol, hexene-1, γ-picoline and the activated catalyst contained in the autoclave was heated at a temperature of 185° through 190° C. to form a homogeneous solution. In the case where a reaction was carried out at a temperature of 185° through 190° and under a total pressure of about 250 kg/cm$^2$G, by pressurizing the autoclave with carbon monoxide, the reaction occurred through the course of the reaction as illustrated in curve I, of FIG. 4. In addition, in the case where additional hexene-1 was added to the autoclave, in such an amount that the molar ratio of the total hexene-1 to the pentaerythritol was 8, after the reaction was effected for 2.5 hours, the reaction was continued through the course of the reaction as illustrated in curve II, of FIG. 4, while a homogeneous solution state was maintained. After the completion of the reaction, the reaction mixture was cooled at a room temperature and carbon monoxide was purged. Homogeneous solution containing no unreacted pentaerythritol was obtained. The resultant esters were separated from the reaction mixture. According to gas chromatography, 98.2% of pentaerythritol tetraheptanoate was contained in the esters and the remainder was triesters and diesters. Furthermore, in the case where the autoclave was charged with pentaerythritol, hexene-1, pyridine and the above-mentioned activated catalyst solution in such amounts that the molar ratio of the hexene-1 to the pentaerythritol was 4, the molar ratio of the pyridine to pentaerythritol was 7.1 and, further, the ratio of the cobalt (in terms of metallic cobalt) to pentaerythritol was 0.12 (gram atom/mol) and the mixture was heated at a temperature of 185° through 190° C., a homogeneous solution was obtained. When a reaction was started at a temperature of 185° through 190° and under a total pressure of 250 kg/cm$^2$G after carbon monoxide was charged, the reaction occurred through a course of reaction as illustrated in curve III, of FIG. 4. After the reaction was carried out for 2 hours when additional hexene-1 was added into the autoclave in such an amount that the molar ratio of the total hexene-1 to the pentaerythritol was 8, the reaction was continued through a course of reaction as illustrated in curve IV, of FIG. 4, while a homogeneous solution state was maintained. The resultant esters were separated from the reaction mixture. As a result of the analysis, 98.5% of pentaerythritol tetraheptanoate was contained in the esters and the remainder was triesters and diesters.

As will be understood from the above described examples, the esterification reaction can be advantageously carried out in a solution state by the additional charge of olefins. When the total amount of the olefin was charged into the autoclave at the beginning of the reaction in the above-mentioned examples, the pentaerythritol was separated from the reaction system as a separate phase.

In accordance with this invention, the esterification reaction can be carried out in a manner similar to those of the conventional processes, except that the charge amounts and the charge procedures of the polyols, the pyridine bases and the olefins are different.

The polyols employed as an alcohol reactant in the present invention include pentaerythritol and polypentaerythritols, such as dipentaerythritol, tripentaerythritol and the like, which can be obtained by the reaction of acetaldehyde and formaldehyde. These polyols are introduced into a reaction zone in the form of a solution thereof in pyridine bases. The solubility of the polyols in the pyridine bases remarkably increases with an increase of a temperature, as shown in FIG. 1. In the region under the line in FIG. 1, a homogeneous solution is formed, whereas, in the region above the line in FIG. 1, phase separation of the polyols occurs in the system. Thus, a solution of polyols in pyridine bases is prepared by heating it to a cetain temperature depending upon the desired concentration of the solution.

The olefins employed in this invention include those having at least 4 carbon atoms, and preferably, linear monoolefins having 4 through 10 carbon atoms, and more preferably, linear α-olefins having 4 through 10 carbon atoms. Typical examples of such olefins are 1-butene, 1-pentene, 1-hexene, 1-heptene, 1-octene, 1-nonene, 1-decene, 2-pentene, 2-hexene, 2-heptene, 2-octene, 3-hexene and 3-heptene.

Figure 2:
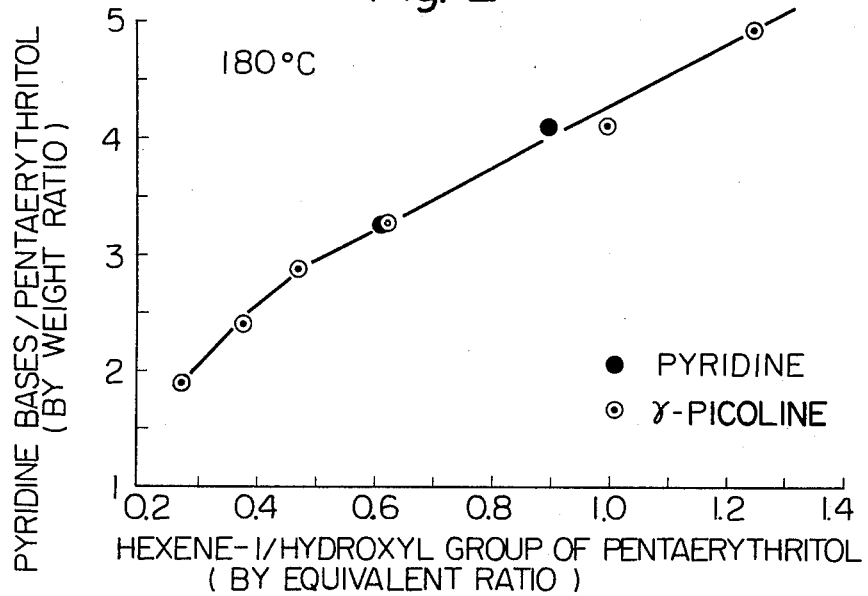
FIG. 2 is a graph illustrating the relationship between the solubility of pentaerythritol in pentaerythritol-pyridine bases-hexene-1 and an equivalent ratio of hexene-1 to the hydroxyl groups of pentaerythritol at a temperature of 180° C.

In accordance with this invention, a portion of the olefins to be used in the esterification reaction of the polyols is fed, together with a solution of the polyols in pyridine bases, to one end (i.e. inlet) of a reaction zone, and the remainder is fed to the middle or intermediate portion of the reaction zone. By the term "the middle portion of the reaction zone", as used herein, is meant the portion where the pentaerythritol is dissolved and phase separation does not occur by the addition of the remainder of the olefins. For example, in the case where the remainder of the olefins is added at one time, it means the portion where the conversion of polyols is 20% or more, and in the case where the remainder is added at two or more times, it means the portion where the conversion of polyols is 15% or more. The divisional addition of the olefins to the reaction zone effectively obviates the above-mentioned problems derived from the phase separation of the polyols in the reaction zone. Since the rate of the esterification reaction largely depends on the ratio of the olefins to the hydroxyl groups of the polyols, at least 0.4 equivalent, and preferably 0.5 or more, of the olefins, based on 1.0 equivalent of the hydroxyl groups of the polyols, must be fed, together with the solution of the pyridine bases, to one end of the reaction zone, in order to smoothly effect the esterification reaction over the entire reaction zone. However, when the charge amount of the olefins becomes too large, the charge amount of the pyridine bases must be increased in order to prevent the phase separation of the polyols in that portion of the reaction zone. For this reason, the charge amount of the olefins which are fed together with the solution of the pyridine bases is preferably not more than 1.1 equivalent, based on 1.0 equivalent of the hydroxyl groups of the polyols. The correlation between the solubility of the pentaerythritol in the pentaerythritol-pyridine bases hexene-1 and the equivalent ratio of hexene-1 to the hydroxyl groups of pentaerythritol at 180° C. is shown in FIG. 2. In the region above the curve of FIG. 2, a homogeneous solution is formed, whereas, in the region under the curve in FIG. 2, the phase separation of the polyols occurs in the system.

In accordance with this invention, the remainder of the olefins is devisionally fed to one or more portions of the middle of the reaction zone so as not to cause the phase separation of the polyols. At least one-third and more preferably, from 45 to 80% by weight, of the total amount of the olefins to be used in the esterification reaction is preferably introduced into the middle portion or portions of the reaction zone. If the amount of the olefins which are introduced into the middle of the reaction zone is less than one-third of the total amount of the olefins, the productivity per unit volume of the reactor unpreferably decreases due to the down of the reaction rate. The total amount of the olefins which are introduced into the reaction zone is generally within the range of from 1.3 to 4 equivalents and, preferably, within the range of from 1.5 to 3 equivalents, based on 1.0 equivalent of the hydroxyl groups of the polyols. The ratio of the olefin to the hydroxyl groups of the polyols influences the yield of the desired full esters of the polyols. If the total amount of the olefin is less than 1.3 equivalent based on 1.0 equivalent of the hydroxyl groups of the polyols, the full esters of the polyols cannot be obtained at a high yield. Contrary to this, if the total amount of the olefin is more than 4 equivalents based on 1.0 equivalent of the hydroxyl groups of the polyols, it is not preferable from the economical point of view since the productivity per unit volume of the reactor decreases. According to this invention, since the olefins are additionally introduced into one or more middle portions of the reaction zone wherein the esters of the polyols are partially formed and, therefore, the solubility of the polyols increases, the esterification reaction can be smoothly carried out, without causing problems due to the phase separation of the polyols, even when the olefins are fed at a high ratio with respect to the hydroxyl groups of the polyols.

The catalysts used in the esterification reaction of the present invention comprise, as a principal constituent, cobalt. Cobalt carbonyl compounds, such as dicobalt octacarbonyl, and any cobalt-containing compounds which are capable of forming cobalt carbonyl compounds in the presence of carbon monoxide can be employed in the present invention. Such cobalt-containing compounds include, for example, cobalt oxides, cobalt hydroxides, cobalt carbonates, cobalt salts of aliphatic acids, especially, those having 1 to 18 carbon atoms and the like. More preferred cobalt compounds are cobalt carbonyl compounds or cobalt salts of aliphatic acid, especially, having 5 to 12 carbon atoms. The amount of the cobalt catalyst used in the present invention can be varied over a wide range, but will generally be within the range of from 0.001 to 0.1 gram atom and preferably, within the range of from 0.01 to 0.05 gram atom, based on 1.0 equivalent of the hydroxyl groups of the polyols. Although the cobalt compounds can be directly introduced into the reaction zone, they are preferably introduced into the reaction zone in the form of the activated catalysts which are previously prepared by reacting the cobalt compounds with carbon monoxide in pyridine bases. It is believed that the catalysts are of complex forms in which the pyridine bases are coordinated to the cobalt carbonyls.

The pyridine bases which are employed, as solvents for the polyols and also as ligands for the catalysts, in the present invention include, for example, pyridine and its derivatives having lower alkyl substituents, such as $\beta$-picoline, $\gamma$-picoline, 4-ethylpyridine, 4-vinylpyridine and the like.

In order to prevent the inhibition of the esterification reaction derived from the phase separation of the polyols in the solution thereof in the pyridine bases, which separation is caused by the addition of the olefins to one end of the reaction zone, the amount of the pyridine bases should be at least 40% by weight, and preferably, 45% by weight or more of the total amount of the polyols, the pyridine bases and the olefins which are introduced into one end of the reaction zone. As will be understood from FIG. 2, in order to form a homogeneous solution of polyols, pyridine bases and olefins, when the amount of the olefins is increased, the amount of the pyridine bases must be increased approximately in proportion to the increase in the amount of the olefins. The most reliable method for preventing the phase separation of the polyols in the reaction zone is that the polyols, the pyridine bases and olefins are fed in such a composition as forms a homogeneous solution at a temperature of the reaction zone. However, the present inventors have surprisingly found that, even when a composition of the polyols, the pyridine bases and the olefins does not form a homogeneous solution in accordance with the correlation as shown in FIG. 2, the esterification reaction smoothly takes place so long as the above-mentioned ratio of the pyridine bases is 40% by weight or more and, preferably, 45% by weight or more. Although the detailed reason for this is not clear, it is believed that the solubility of the polyols could be increased by the mixing of the polyols with the resultant esters present in the reaction zone.

On the other hand, in the case where the ratio of the amount of the pyridine bases to the total initial feeds becomes too large, the yield of the esters per unit volume of the reactor decreases as mentioned hereinabove. Further, in the case where the ratio of the pyridine bases to the cobalt catalysts is too large, the catalytic activity decreases and, therefore, the yield of the desired full esters of the polyols decreases. For these reasons, the amount of the pyridine bases should be not more than 70% by weight and, preferably, 65% by weight or less, of the total amount of the polyols, the pyridine bases and the olefins which are introduced into one end of the reaction zone.

The amount of the pyridine bases which are contained in the activated catalysts must be taken into account when the above-mentioned amount ratio of the pyridine bases in the feed reactants is calculated.

According to this invention, since the esterification reaction takes place in a substantially homogeneous solution state, a mechanical agitation is not required in a reactor and, therefore, reactors provided with no mechanical type agitator, such as a bubble column or a gas sparged column, can be advantageously used.

Figure 3:
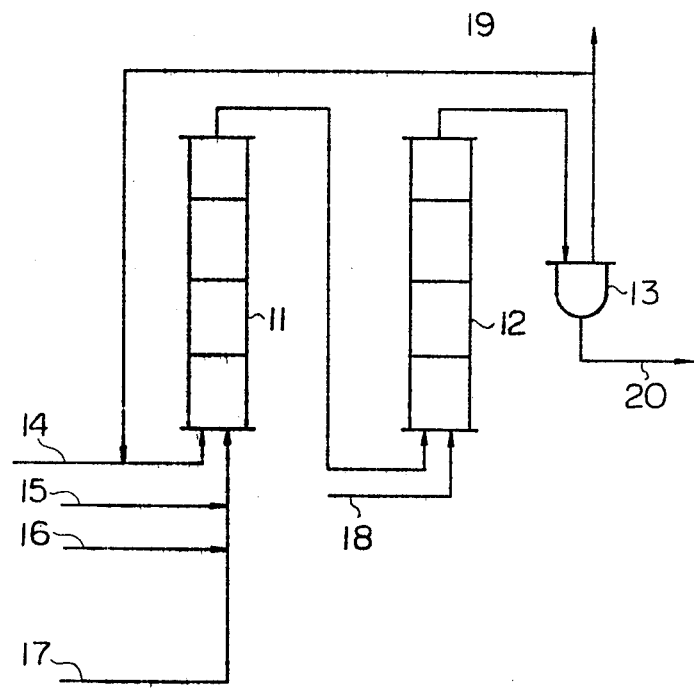
FIG. 3 is a flow diagram illustrating one embodiment of the process flow according to this invention.

One typical embodiment of the process flow according to the present invention is illustrated in FIG. 3. Referring to FIG. 3, two bubble columns 11 and 12 are connected in series. Carbon monoxide, olefin, a solution of polyols in pyridine bases and a catalyst solution are continuously introduced, through feed lines 14, 15, 16 and 17, respectively, into the bottom of the first column 11 and, an additional olefin 18 is fed to the bottom of the second column 12. The reaction mixture discharged from the top of the second column 12 is separated into a gas phase and a liquid phase in a conventional gas-liquid separator 13. The gas phase is recycled, through a line 19, to the bottom of the first column 11, while a portion of the gas phase is discharged out of the system in order to prevent the accumulation of the impurities in the system. On the other hand, the liquid phase is transferred through a line 20 to a conventional post-treatment step (not shown in FIG. 3), wherein the desired full esters of the polyols, which are a principal product of the present process, are obtained. The bubble columns 11 and 12 may be vacant columns or columns in which one or more appropriate conventional partition plates are provided so that piston flow properties are imparted to the reactant mixture.

In addition, instead of the two bubble columns 11 and 12, only one bubble column can be used and the additional olefins are fed to the middle portion of the column. Furthermore, three or more bubble columns can also be used.

Although the reaction temperature and pressure condition are not critical, the temperature of the reactors can be generally in the range of from 140° to 300° C., and preferably, in the range of from 160° to 250° C., and the pressure of the reactors can be generally 50 though 400 kg/cm$^2$G, and preferably, 100 through 300 kg/cm$^2$G. In general the pressure is mostly made of carbon monoxide. Carbon monoxide may contain other inert gases such as methane, nitrogen and carbon dioxide as impurities in this esterification process. However, since the presence of hydrogen in the carbon monoxide causes an undesirable side reaction, the hydrogen content of the carbon monoxide is preferably 5% by volume or less.

According to this invention, full esters of polyols can be continuously obtained, at a high yield, from polyols, olefins and carbon monoxide.

This invention will now be further illustrated by but is not limited to the following Example.

EXAMPLE

A first bubble column (2 liter internal volume) and a second bubble column (3 liter internal volume) were placed, in series, as shown in FIG. 3. 100 g/hr of hexene-1, 250 g/hr of a homogeneous solution of pentaerythritol in γ-picoline (the weight ratio of pentaerythritol to γ-picoline was 1:2.7), 65 g/hr of an activated catalyst solution and 67 Nl/hr of carbon monoxide were continuously introduced into the bottom of the first bubble column and, further, 230 g/hr of additional hexene-1 was continuously fed to the bottom of the second bubble column. The activated catalyst was previously prepared by heating a 1.3:9:2 mixture (by mol ratio) of cobalt octanoate, γ-picoline and water in an autoclave, with stirring, to a temperature of 170° C. and, then, by stirring the mixture in the presence of carbon monoxide, for 2 hours, under a total pressure of 200 kg/cm$^2$G.

The first and second bubble columns were maintained at a temperature of approximately 190° C. and under a pressure of approximately 200 kg/cm$^2$G. The reaction mixture discharged from the top of the second column was cooled and separated into a gas and liquid phase. The gas phase was discharged out of the system and the liquid phase was recovered.

In a long run test, the pentaerythritol tetraheptanoate was obtained at a yield of 98% without causing inhibition of the esterifaction reaction derived from the precipitation of the pentaerythritol. Contrary to this, in a case that the total amount of the hexene-1 was introduced into the bottom of the first column, the operation became impossible within only a short time of period due to the precipitation of the pentaerythritol.

What we claim is:

1. A process for continuously producing full esters of polyols comprising reacting (i) at least one polyol selected from pentaerythritol and polypentaerythritols, (ii) from 1.3 to 4 equivalents based on 1.0 equivalent of the hydroxyl groups of the polyol of at least one olefin having at least 4 carbon atoms, and (iii) carbon monoxide, in the presence of a catalyst containing at least one cobalt carbonyl and at least one pyridine base, said reaction being carried out by:

continuously introducing a solution of said at least one polyol in said at least one pyridine base, the olefin in an amount of from 0.4 to 1.1 equivalent based on 1.0 equivalent of the hydroxyl groups of the polyol, the cobalt carbonyl and the carbon monoxide, into one end of a reaction zone the amount of the pyridine base being within a range of from 40 to 70% by weight based on the total amount of the pyridine base, the polyol and the olefin;

introducing the remainder of the olefin into at least one middle portion of the reaction zone where the esterification of the polyol is 15% or more; and continuously withdrawing the resultant reaction mixuture from the other end of the reaction zone.

2. A process as claimed in claim 1, wherein the amount of said at least one pyridine base is within a range of from 45 to 65% by weight based on the total amount of the pyridine base, the polyol and the olefin which are introduced into said one end of the reaction zone.

3. A process as claimed in claim 1, wherein the amounts of said at least one pyridine base, the ployol and olefin which are introduced into said one end of the reaction zone are such that said constituents form a homogeneous solution at the reaction zone temperature.

4. A process as claimed in claim 1, wherein the amount of the olefin introduced into the middle of the reaction zone is one half or more of that of the olefin introduced into said one end of the reaction zone.

5. A process as claimed in claim 1, wherein said reaction is carried out in at least one bubble column.

6. A process as claimed in claim 1, wherein the remainder of olefin is introduced into at least one middle portion of the reaction zone where the esterification of polyol is 20% or more.

7. A process as claimed in claim 1, wherein the reaction temperature is in the range of from 140° to 300° C.

8. A process as claimed in claim 1, wherein the reaction pressure is in the range of from 50 to 400 kg/cm$^2$G.

9. A process as claimed in claim 1, wherein the amount of olefin introduced into said one end of the reaction zone is from 0.5 to 1.1 equivalent based on 1.0 equivalent of the hydroxyl groups of the polyol.

* * * * *